United States Patent [19]

Barton et al.

[11] Patent Number: 4,501,701

[45] Date of Patent: Feb. 26, 1985

[54] 20-ISOCYANO-$\Delta^{17(20)}$-STEROIDS

[75] Inventors: Derek H. R. Barton; William B. Motherwell; Sammir Z. Zard, all of Gif sur Yvette, France

[73] Assignee: Roussel Uclaf, Paris, France

[21] Appl. No.: 281,552

[22] Filed: Jul. 7, 1981

[30] Foreign Application Priority Data

Jul. 15, 1980 [FR] France ............................ 80 15603

[51] Int. Cl.³ .............................................. C07J 1/00
[52] U.S. Cl. .............................. 260/397.4; 260/397.5; 260/940; 260/944
[58] Field of Search ............... 260/397.4, 397.5, 940, 260/944

[56] References Cited

U.S. PATENT DOCUMENTS 4,251,450  2/1981  Krbechek ...................... 260/397.4

Primary Examiner—Elbert L. Roberts
Attorney, Agent, or Firm—Charles A. Muserlian

[57] ABSTRACT

Novel 20-isocyano-$\Delta^{17(20)}$-steroids of the formula

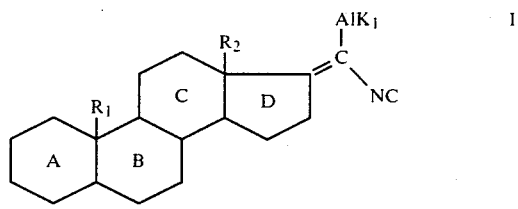

wherein $R^1$ is selected from the group consisting of (1) hydrogen, (2) alkyl of 1 to 4 carbon atoms optionally substituted with a member of the group consisting of halogen, an oxygen function and a nitrogen function and (3) alkenyl and alkynyl of 2 to 4 carbon atoms, $R_2$ is alkyl of 1 to 4 carbon atoms, $Alk_1$, is alkyl of 1 to 8 carbon atoms and the A,B,C, and D rings may contain one or more double bonds and may be optionally substituted with at least one member of the group consisting of —OH, =O, halogens, alkyl and alkoxy of 1 to 4 carbon atoms and alkenyl and alkynyl of 2 to 4 carbon atoms and a process for their preparation and their use to prepare 17α-ol-20-keto steroids.

18 Claims, No Drawings

20-ISOCYANO-Δ$^{17(20)}$-STEROIDS

STATE OF THE ART

Raggio et al [J. Org. Chem., Vol. 41, No. 10 (1976), p. 1873–75] describe the preparation of progesterone from dehydro epiandrosterone which includes the reaction of the 17-keto-androstone compound with 2-(diethylphosphono)-propionitrile.

OBJECTS OF THE INVENTION

It is an object of the invention to provide the novel 20-isocyano-Δ$^{17(20)}$-steroids of formula I and a process for their preparation and novel intermediates therefore.

It is another object of the invention to provide a novel process for the preparation of 17α-ol-20-ketosteroids.

These and other objects and advantages of the invention will become obvious from the following detailed description.

THE INVENTION

The novel compounds of the invention are 20-isocyano-Δ$^{17(20)}$-steroids of the formula

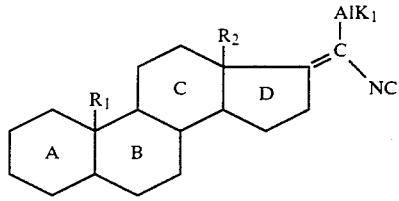

wherein $R_1$ is selected from the group consisting of (1) hydrogen, (2) alkyl of 1 to 4 carbon atoms optionally substituted with a member of the group consisting of halogen, an oxygen function and a nitrogen function and (3) alkenyl and alkynyl of 2 to 4 carbon atoms, $R_2$ is alkyl of 1 to 4 carbon atoms, $AlK_1$, is alkyl of 1 to 8 carbon atoms and the A,B,C, and D rings may contain one or more double bonds and may be optionally substituted with at least one member of the group consisting of —OH, =O, halogen, alkyl and alkoxy of 1 to 4 carbon atoms and alkenyl and alkynyl of 2 to 4 carbon atoms.

Examples of $R_1$ are alkyl such as methyl and ethyl; alkyl substituted with an oxygen function such as hydroxymethyl, hydroxyethyl, formyl and acetyl; alkyl substituted with a nitrogen function such as aminomethyl, cyano and aminoethyl; alkyl substituted with a halogen such as —CH$_2$Hal where Hal is chlorine, fluorine, bromine or iodine; alkenyl such as vinyl and allyl; and alkynyl such as ethynyl. Examples of $R_2$ are methyl and ethyl and examples of $AlK_1$ are methyl, ethyl, n-propyl and isopropyl.

When the A,B,C and D rings contain one or more double bonds, the double bonds are preferably in the 1(2), 3(4), 4(5) or 9(11) positions or in a system of conjugated bonds in the 3(4) and 5(6) or 4(5) and 6(7) or 1(2) and 4(5) positions or an aromatic system of three double bonds in the 1,3 and 5 positions or a system of three double bonds in the 1(2), 4(5), 6(7) positions.

When the A,B,C and D rings are substituted with a hydroxyl group, it is preferably in the 3- or 11-positions and keto substituents are preferably in the 3- or 11-positions. Halogen substituents such as fluorine, chlorine or bromine are preferably in the 6- or 9α-positions and the preferred alkyl substituents are methyl or ethyl in the 2-, 6-, 7-,16α- or 16β-positions and the preferred alkoxy substituents are methoxy or ethoxy in 3 or 11β-positions. The preferred alkenyl substituents are vinyl or allyl in the 11β-position and the preferred alkynyl substituent is 11β-ethynyl.

Preferred compounds of formula I are those wherein $R_2$ is methyl and those wherein $R_1$ is hydrogen or methyl and those wherein $AlK_1$ is methyl, especially 3-methoxy-20-isocyano-Δ$^{3,5,17(20)}$-pregnatriene.

Particularly preferred compounds of the invention are compounds of the formula

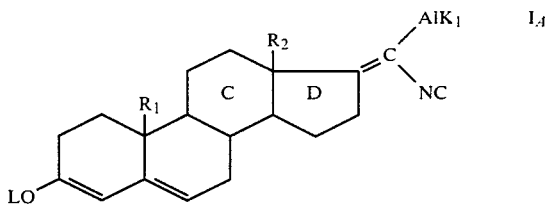

wherein L is a hydroxy protective group, $R_1$, $R_2$ and $AlK_1$ have the above definitions and the C and D rings may contain at least one double bond and may be substituted with at least one member of the group consisting of —OH, =O, halogen, alkyl and alkoxy of 1 to 4 carbon atoms and alkenyl and alkynyl of 2 to 4 carbon atoms. Preferred, however, are the compounds of formula $I_A$ wherein the C and D rings do not contain any double bonds.

It is clear to one skilled in the art that the compounds of formula I have a great commercial interest as they can be directly prepared in very good yields from the corresponding 17-keto-steroids in a simple and economical manner and can further be transformed into the corresponding 17α-ol-20-one steroids in very good yields in a simple and economical manner.

For example, 3-methoxy-20-isocyano-Δ$^{3,5,17(20)}$-pregnatriene can be used to prepare 17α-hydroxy-progesterone or -Δ$^4$-pregnene-17α-ol-3,20-dione which is a very well known industrial product for steroid synthesis. The compounds of formula I are useful for the preparation of a very large number of steroids by analogous methods such as 21-desoxy-cortisone, 21-desoxy-cortisol, 21-desoxy-prednisolone and 21-desoxy-prednisone.

The novel process for the invention for the preparation of the compounds of formula I comprises reacting a compound of the formula

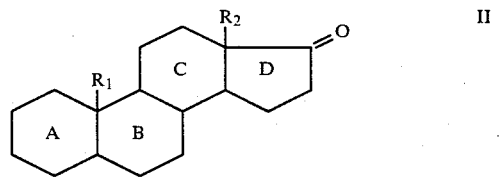

wherein $R_1$, $R_2$, A,B,C and D have the above definitions with a compound of the formula

wherein $AlK_1$ has the above definition and $AlK_2$ is alkyl of 1 to 8 carbon atoms to obtain the corresponding compounds of formula I.

Preferably, AlK$_2$ is ethyl and the reaction is effected in an aprotic polar solvent in the presence of a strong base.

A preferred mode of the process of the invention for the preparation of a compound of formula I$_A$ comprises reacting a compound of the formula

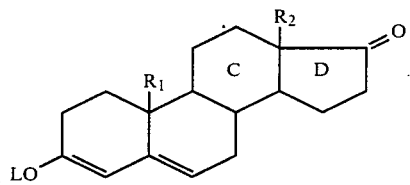

with a compound of formula III to obtain the corresponding compound of formula I$_A$.

It is especially preferred to react a compound of formula II or II$_A$ with a compound of formula III wherein AlK$_1$ is methyl to obtain the corresponding compound of formula I or I$_A$ wherein AlK$_1$ is methyl. Most preferred is the reaction of 3-methoxy-$\Delta^{3,5}$-androstadiene-17-one with diethyl 1-isocyanoethyl-phosphonate to obtain 3-methoxy-20-isocyano-$\Delta^{3,5,17(20)}$-pregnatriene.

Another novel process of the invention is the preparation of a compound of formula III comprising reacting a compound of the formula

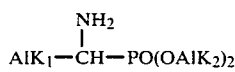

wherein AlK$_1$ and AlK$_2$ have the above definitions with a formylation agent to obtain a compound of the formula

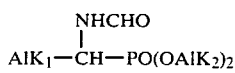

and reacting the latter with phosgene or phosphorus oxychloride to obtain the corresponding compound of formula III.

Preferably, the formylation agent is formic acid or one of its derivatives such as mixed anhydride of formic acid and acetic acid and the reaction of the compound of formula V with phosgene or phosphorus oxychloride is effected in the presence of triethylamine or other tertiary amine.

The compounds of formulae III and V are novel and are an object of the invention. Especially preferred intermediates are diethyl 1-isocyanoethyl-phosphonate and diethyl 1-(N-formylamino)-ethyl-phosphonate.

The compounds of formula IV used as starting materials are known compounds or may be prepared by the process of Chalmers et al, J.A.C.S., Vol. 75 (1953), p. 5278.

A process of the invention is that for the preparation of 17α-ol-20-keto-steroids comprising subjecting a compound of formula I to selective hydration of the isocyano group in an acid medium, epoxidation, action of an acid agent and then saponification to obtain a compound of the formula

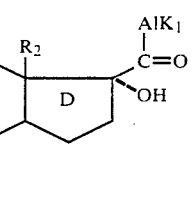

wherein R$_1$, R$_2$, A,B,C and D have the above definitions. In a preferred modification, a compound of formula I$_A$ is reacted to obtain a compound of the formula

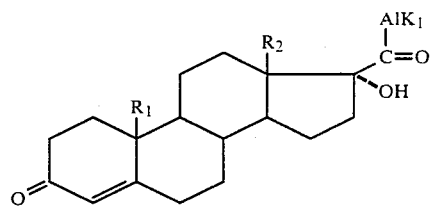

Most preferred is the reaction of 3-methoxy-20-isocyano-$\Delta^{3,5,17(20)}$-pregnatriene to form $\Delta^4$-pregnene-17α-ol-3,20-dione.

In a preferred mode of the latter process, the selective hydration in an acid medium is effected with acetic acid, chloroacetic acid, propionic acid, oxalic acid or formic acid and the epoxidation is effected with a peracid such as m-chloroperbenzoic acid, perphthalic acid, peracetic acid or performic acid. The acid agent is an acid such as acetic acid, propionic acid, oxalic acid or chloroacetic acid in an aqueous medium and the saponification is effected with a strong base such as sodium hydroxide, potassium hydroxide or a carbonate such as sodium bicarbonate or potassium bicarbonate.

In the following examples there are described several preferred embodiments to illustrate the invention. However, it is to be understood that the invention is not intended to be limited to the specific embodiments.

EXAMPLE 1

3-methoxy-20-isocyano-$\Delta^{3,5,17(20)}$-pregnatriene

STEP A: Diethyl 1-(N-formylamino)-ethyl-phosphonate

A mixture of 3.6 g of diethyl α-aminoethyl-phosphonate prepared by the process of Chalmers et al, J.A.C.S., Vol 75 (1953), p. 5278 and 2 g of formylacetic acid anhydride stood overnight at room temperature and was then heated at 120° C. under a pressure of 0.5 to 1 mm Hg for 15 to 20 minutes. The residue was distilled to obtain pure diethyl 1-(N-formylamino)-ethyl-phosphonate with a boiling point of 148°~150° at 0.5 mm Hg which was used as is for the next step.

NMR Spectrum (deuterochloroform): Peaks at 8.15 ppm (1-hydrogen of

at 7.80 ppm (hydrogen of —NH); at 1.1–1.6 ppm (hydrogen of —CH$_3$, 9H).

STEP B: Diethyl 1-isocyanoethyl-phosphonate

A solution of 5.5 g of phosgene in 40 ml of dichloromethane was added over 30 minutes at 35°~40° C. to a mixture of 9.85 g of the product of Step A, 16 ml of triethylamine and 25 ml of dichloromethane and the mixture was kept at 35° C. for 2 hours. The dichloromethane was evaporated under reduced pressure and the residue was extracted with a 1-3 ether-pentane mixture. The extract was filtered and the solvent was evaporated. The residue was distilled to obtain diethyl 1-isocyanoethyl-phosphonate with a boiling point of 82°-84° at 0.5 mm Hg.

NMR Spectrum (deuterochloroform): Peaks at 3.6-4.4 ppm (5H multiplets, hydrogens of methyl and methylene); at 1.2-1.8 ppm (9H, multiplet).

STEP C: 3-methoxy-20-isocyano-$\Delta^{3,5,17(20)}$-pregnatriene

A solution of 6 g of the product of Step B in 20 ml of dimethoxyethane was added with stirring at 0° to 5° C. under a nitrogen atmosphere over 40 to 50 minutes to a suspension of 6 g of 21% potassium hydride in oil previously washed with pentane in 20 ml of dimethoxyethane and then 900 mg of 3-methoxy-$\Delta^{3,5}$-androstadiene-17-one were added to the mixture. The mixture was stirred at 0° C. for 4 hours and overnight at room temperature and was then poured into an aqueous saturated sodium chloride solution. The mixture was extracted with ether and the ether phase was washed with water and evaporated to dryness. The residue was chromatographed over silica gel and was eluted with a 92-8 hexane-ether mixture to obtain 915 mg (90.5% yield) of 3-methoxy-20-isocyano-$\Delta^{3,5,17(20)}$-pregnatriene which after crystallization from hexane melted at 114°~134° C.

NMR Spectrum (deuterochloroform): Peaks at 5.20 ppm (1-hydrogen, large H at 6); at 5.10 ppm (1-hydrogen, large H at 4); at 3.50 ppm (3H singulet-hydrogens of —OCH$_3$); at 1.85 ppm (3H singulet hydrogens of 21-CH$_3$); at 1.22 ppm (3H singulet-hydrogens of 13-CH$_3$); at 0.98 ppm (3H singulet hydrogens of 10-CH$_3$).

EXAMPLE 2

$\Delta^4$-pregnene-17$\alpha$-ol-3,20-dione or 17$\alpha$-hydroxy-progesterone

A solution of 35-40 mg of formic acid in 8 ml of dichloromethane was added to a solution of 90 mg of 3-methoxy-20-isocyano-$\Delta^{3,5,17(20)}$-pregnatriene in 2 ml of dichloromethane and the mixture stood overnight at room temperature. 150 mg of m-chloroperbenzoic acid were added to the mixture and 5 drops of dimethylsulfide were added thereto after about 15 minutes to destroy excess peracid. 9 ml of acetic acid and 3 ml of water were added to the mixture which was then heated in a water bath for 90 minutes to evaporate the dichloromethane and was then poured into water. The mixture was extracted with ether and the organic phase was washed with water and then with aqueous 5% sodium carbonate solution, dried and evaporated to dryness under reduced pressure. The residue was dissolved in 10 ml of ethanol and 4 ml of 0.5N sodium hydroxide solution were added thereto. The mixture was heated in a water bath for 5 to 10 minutes and was diluted with 20 ml of water. The mixture was extracted with dichloromethane and the organic phase was dried and evaporated to dryness to obtain 77 mg (88% yield) of $\Delta^4$-pregnene-17$\alpha$-ol-3,20-dione or 17$\alpha$-hydroxy-progesterone with a melting point of 221°~223° C. and a specific rotation of $[\alpha]_D^{20} = +98°$ (in acetone).

Various modifications of the products and processes of the invention may be made without departing from the spirit or scope thereof and it should be understood that the invention is intended to be limited only as defined in the appended claims.

What is claimed is:

1. A 20-isocyano-17(20)-steroid of the formula

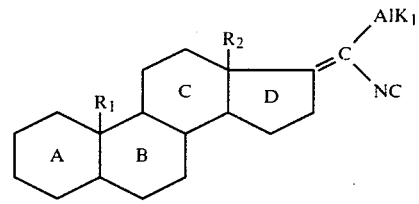

wherein R$_1$ is selected from the group consisting of (1) hydrogen, (2) alkyl of 1 to 4 carbon atoms optionally substituted with a member of the group consisting of halogen, hydroxy, carbonyl, amino and cyano and (3) alkenyl and alkynyl of 2 to 4 carbon atoms, R$_2$ is alkyl of 1 to 4 carbon atoms, AlK$_1$ is alkyl of 1 to 8 carbon atoms and the A,B,C and D rings may contain one or more double bonds and may be optionally substituted with at least one member of the group consisting of —OH, =O, halogens, alkyl and alkoxy of 1 to 4 carbon atoms and alkenyl and alkynyl of 2 to 4 carbon atoms.

2. A compound of claim 1 wherein R$_2$ is —CH$_3$.

3. A compound of claim 1 or 2 wherein R$_1$ is selected from the group consisting of hydrogen and methyl.

4. A compound of claim 1 having the formula

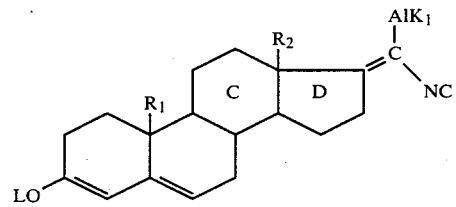

wherein L is a hydroxy protecting group.

5. A compound of claim 4 wherein the C and D rings are saturated.

6. A compound of claim 1 or 4 wherein AlK$_1$ is —CH$_3$.

7. A compound of claim 1 which is 3-methoxy-20-isocyano-$\Delta^{3,5,17,(20)}$-pregnatriene.

8. A compound having a formula selected from the group consisting of

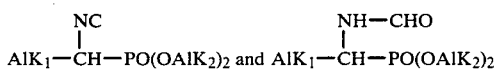

wherein AlK$_1$ and AlK$_2$ are individually alkyl of 1 to 8 carbon atoms.

9. A compound of claim 8 which is diethyl 1-(N-formylamino)-ethyl-phosphonate.

10. A compound of claim 8 which is diethyl 1-isocyanoethyl-phosphonate.

11. A process for the preparation of a compound of claim 1 comprising reacting a compound of the formula wherein $R_1$, $R_2$, A,B,C and D have the above definitions with a compound of the formula

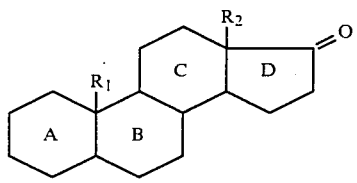

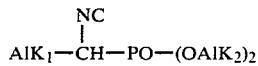

wherein $AlK_1$ has the above definition and $AlK_2$ is alkyl of 1 to 8 carbon atoms to obtain the corresponding compound of claim 1.

12. A process of claim 11 wherein the compound reacted with the compound of formula III has the formula

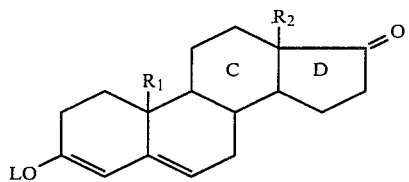

wherein $R_1$, $R_2$, C and D have the above definition and L is a hydroxy protecting group to obtain the corresponding compound of claim 4.

13. The process of claim 11 or 12 wherein $AlK_1$ is $-CH_3$.

14. The process of claim 11 wherein 3-methoxy-$\Delta^{3,5}$-androstadiene-17-one is reacted with diethyl 1-isocyanoethylphosphonate to obtain 3-methoxy-20-isocyano-$\Delta^{3,5,17(20)}$-pregnatriene.

15. A process for the preparation of a compound of the formula

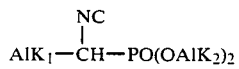

wherein $AlK_1$ and $AlK_2$ are individually alkyl of 1 to 8 carbon atoms comprising reacting a compound of the formula

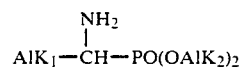

wherein $AlK_1$ and $AlK_2$ have the above definition with a formylation agent to obtain a compound of the formula

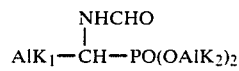

and reacting the latter with phosgene or phosphorus oxychloride to obtain the corresponding compound of formula III.

16. A process for the preparation of a compound of the formula

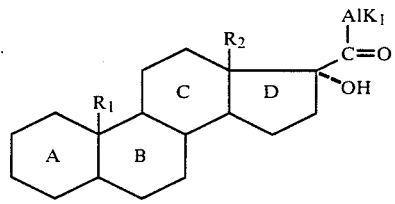

wherein $R_1$, $R_2$, A,B,C and D are defined as in claim 1 comprising subjecting a compound of claim 1 consecutively to selective hydration of the isocyano group in an acid medium, epoxidation, action of an acid agent and then saponification to obtain a compound of the formula VI.

17. The process of claim 16 wherein the compound of claim 4 is reacted to obtain a compound of the formula

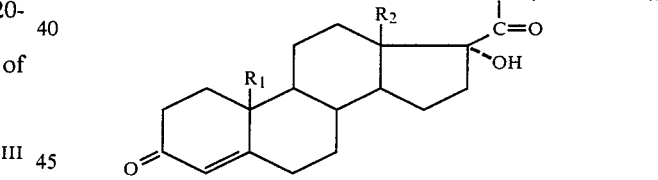

18. The process of claim 16 wherein 3-methoxy-20-isocyano-$\Delta^{3,5,17(20)}$-pregnatriene is reacted to form $\Delta^4$-pregnene-17α-ol-3,20-dione.

* * * * *